United States Patent [19]

Nyi

[11] Patent Number: 5,063,913
[45] Date of Patent: Nov. 12, 1991

[54] ELBOW BRACE AND METHOD FOR PREVENTING OR ATTENUATING TENNIS ELBOW

[76] Inventor: Franklin H. Nyi, 23409 Broadwell Ave., Torrance, Calif. 90502

[21] Appl. No.: 619,620

[22] Filed: Nov. 29, 1990

[51] Int. Cl.$^5$ ............................................... A61F 5/10
[52] U.S. Cl. ........................................ 128/77; 128/165
[58] Field of Search ............... 128/77, 80 C, 165, 402, 128/60, DIG. 15

[56] References Cited

U.S. PATENT DOCUMENTS

| | | |
|---|---|---|
| 3,785,371 | 1/1974 | Lewis . |
| 3,877,426 | 4/1975 | Nirschl ................. 128/165 |
| 3,926,186 | 12/1975 | Nirschl ................. 128/165 |
| 3,934,583 | 1/1976 | Hollingshead et al. ........... 128/77 X |
| 3,970,081 | 7/1920 | Applegate, Jr. . |
| 4,027,666 | 6/1977 | Marx ..................... 128/165 |
| 4,048,991 | 9/1977 | Marx ..................... 128/77 X |
| 4,128,097 | 12/1978 | Bilinsky et al. ........... 128/165 |
| 4,182,318 | 1/1980 | Beige et al. ............ 128/77 |
| 4,191,373 | 3/1980 | Lancellotti ............ 128/77 X |
| 4,299,214 | 11/1981 | Sweitzer ............... 128/165 |
| 4,323,232 | 4/1982 | Terpening . |
| 4,441,493 | 4/1984 | Nirschl ................ 128/165 |
| 4,509,750 | 4/1985 | Last .................... 128/402 X |
| 4,520,798 | 6/1985 | Lewis .................. 128/60 X |
| 4,628,918 | 12/1986 | Johnson, Jr. . |
| 4,632,106 | 12/1986 | Gamm ................. 128/165 |
| 4,763,901 | 8/1988 | Richter ................ 128/77 X |
| 4,807,607 | 2/1989 | Röder ................... 128/77 |
| 4,870,956 | 10/1989 | Fatool et al. ......... 128/165 X |
| 4,905,998 | 3/1990 | Last .................... 128/402 X |

FOREIGN PATENT DOCUMENTS

| | | | |
|---|---|---|---|
| 2632706 | 7/1976 | Fed. Rep. of Germany | 128/165 |
| 2936174 | 3/1981 | Fed. Rep. of Germany | 128/165 |

Primary Examiner—Richard J. Apley
Assistant Examiner—Linda C. M. Dvorak
Attorney, Agent, or Firm—Fulwider, Patton, Lee & Utecht

[57] ABSTRACT

A brace for preventing or attenuating the effects of tennis elbow utilizes a pair of shock absorbing elements that are placed over the arm over the lateral and medial epicondyle of the humerus bone. These shock absorbing elements provide a medium for absorbing a portion of the shock energy and vibration that can travel along the forearm and exit the elbow of a person during physical activity. The elbow brace also includes pressure transmitting elements which are designate to localize pressure directly on the tendon that extends from the extensor digitorum muscle that is attached to the humerus. The other pressure transmitting element can be placed in contact with the arm directly over the tendon of the triceps brachii which is attached to the olecranon of the ulna.

22 Claims, 2 Drawing Sheets

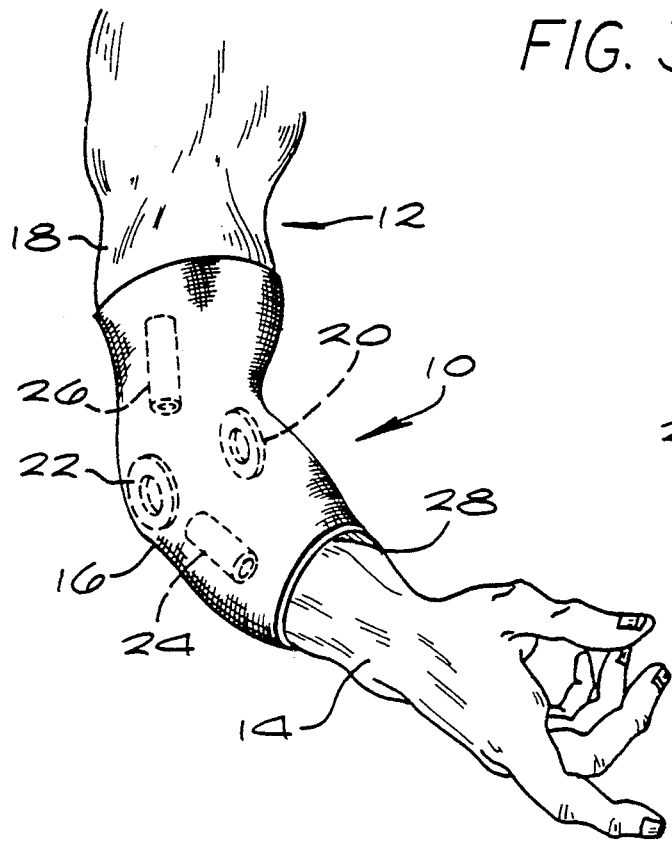
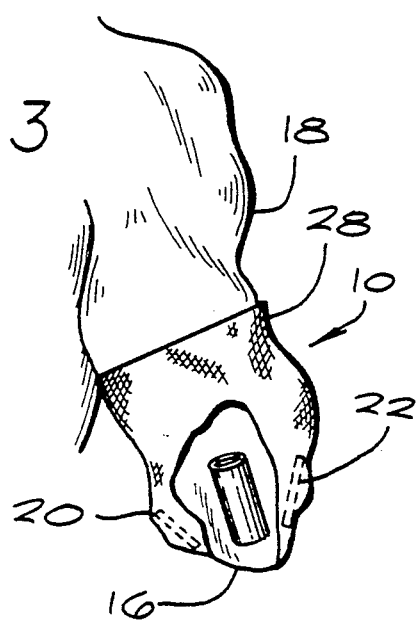
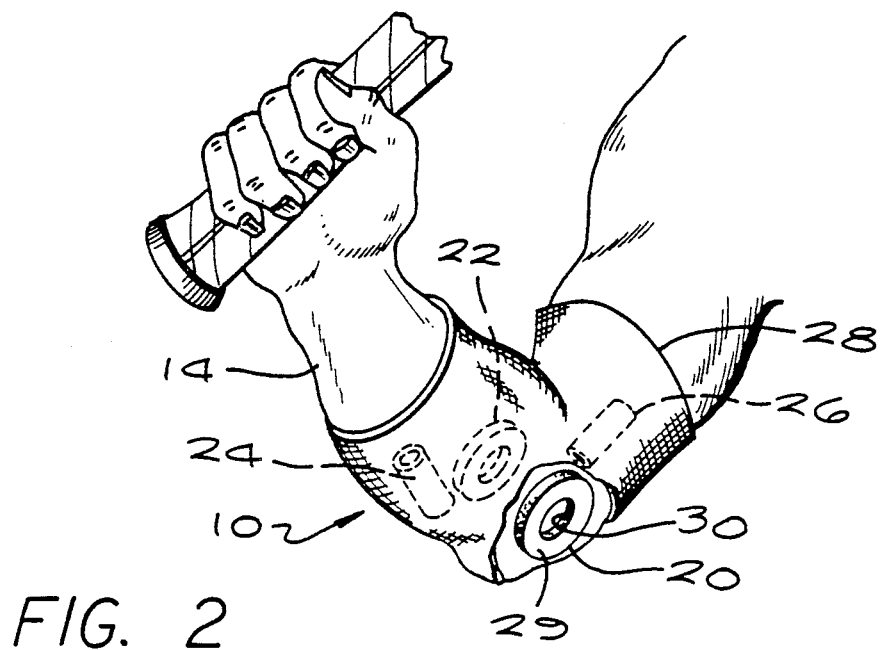

ELBOW BRACE AND METHOD FOR PREVENTING OR ATTENUATING TENNIS ELBOW

BACKGROUND OF THE INVENTION

1. Field of the Invention

The present invention relates generally to arm and elbow braces and, more particularly, to an elbow brace for preventing or attenuating the painful inflammation of the tendons in the elbow, commonly known as "tennis elbow." The present invention accomplishes this through the application of direct pressure on various tendons that are susceptible to abnormal stretching during strenuous athletic activities along with placement of shock absorbing elements around the epicondyle of the humerus bone to absorb and dissipate at least a portion of any shock energy that may travel along the forearm of the user. The invention is also directed to a method for preventing or reducing this condition known as tennis elbow utilizing these same principles.

2. Description of Related Art

Tennis elbow is a commonly used term to describe a painful, medical condition which is characterized by inflammation of the ligaments that connect the two bones of the forearm, the radius and ulna, and inflammation of the tendons of the muscles of the forearm that are attached to the two spurs of the humerus, the medial and lateral epicondyle. Inflammation can also occur to the tendon of the triceps brachii which is attached to the olecranon of the ulna and can also extend to the tissues in the area directly surrounding the medial and lateral epicondyle.

This condition, as the name implies, has been generally associated with the sport of tennis, although it can be experienced by participants in a number of other sporting activities, in which a racket, bat, or other sporting equipment is utilized to strike another object. This condition can also occur in persons who throw objects, such as baseballs, footballs and the like, especially if an abnormal amount of bending and twisting occurs in the arm and elbow during the throw. Also, tennis elbow can occur in non-sports related activities, such as hammering or performing manual labor which requires a high amount of elbow flexure and repetitive motion of the forearm.

The most characteristic symptom of tennis elbow is extreme pain which occurs from continued participation in the physical activity. Pain can also be brought on through simple movement of the forearm, for example, when a person lifts even a light object. The pain resulting with tennis elbow has been most often attributed to the inflammation that occurs to the tendons of the muscles of the forearm which are attached to the medial and lateral epicondyle of the humerus bone. Also, due to the shock that can be generated in the elbow region during physical activities, inflammation to the surrounding tissues can occur and also cause pain. Inflammation of the tendon extending from the triceps brachii to the olecranon also adds to the overall pain suffered by the afflicted person.

Although the cause of tennis elbow and the associated inflammation of the tendons and tissue in the region of the elbow are not completely understood, it appears that the condition is most often excaberated when the participant holds an object and strikes another object with the held object. For example, in the case of an activity such as tennis, the player holds a racket which acts as an outward extension of his own arm. The act of striking a moving ball, which can create quite an impact or force on the head of the racket, causes a shock wave or shock energy to travel along the handle of the racket and in turn along the forearm of the player. The shock energy (and the associated vibration) then propagates up the forearm and along the various muscles and tendons of the forearm until it terminates and dissipates at the elbow. Whenever the ball is hit by the player, shock energy travels up along the muscles of the forearm where it will cause some trauma and stretching of the tendons. In the event that a ball is mishit by the player, an increased amount of shock is created which again travels through the racket down along the forearm where it can do considerably more harm to the tendons and tissues in the elbow.

The shock which travels along the forearm of the player can cause at least some of the tendons attached at the epicondyle to stretch and move outward away from the bone in a phenomena sometimes referred to as "pouching". This phenomenon is especially prevalent to the tendon of the extensor digitorum muscle which is attached to the epicondyle. Since this tendon is somewhat larger than most tendons in the area, the resulting shock and movement of the muscles during the swing of the player's arm causes the tendon to stretch and move outward away from the underlying bone. As a result, continued shock can cause this particular tendon to continue to stretch and "pouch" causing the tendon to enlarge and become inflamed. In some situations, the tendons become so stretched from its original size that surgery must be performed to reduce its size back to the size of a normal tendon. This, of course, is a rare occurrence but shows the damage that the shock energy can inflict on at least one of the tendons of the forearm.

Similar pouching can also occur to the tendon extending from the triceps brachii which is in turn attached to the olecranon of the ulna. This particular tendon can also stretch and pouch resulting in inflammation and its associated discomfort. Prolonged and continuous subjection of this tendon to the shock wave again causes additional stretching and increased pain from inflammation.

Treatment for tennis elbow generally consists of rest which allows the tendons to heal and naturally revert to their original length which also helps to reduce the associated inflammation. To some extent, exercise can be performed to strengthen the muscle and its tendon, however, once the condition begins, it is often difficult to exercise to alleviate tennis elbow. Other treatments include taking anti-inflammatory drugs, such as aspirin and other pain killing drugs along with injections of hydrocortisone and other similar pain-killing medications. In rare and severe cases, as mentioned above, surgery may have to be performed to reduce the length of the stretched tendon.

Other treatment to prevent this condition of tennis elbow is through the wearing of devices which apply pressure around the forearm of the player to prevent some of the movement of the muscles and tendons during the physical activity. Such devices usually are made from an elastic band and velcro straps which apply a radial pressure to the forearm. In many devices, a generalized pressure is applied to the region of the elbow without much attention being given to localizing the pressure to the particular tendons that are more susceptible to the phenomenon of pouching. As a result, these prior art devices provide some means for preventing pouching, but for the most part, only reduce it a small amount. Also, prior art devices have been utilized to apply direct pressure onto the medial and lateral epicondyle to reduce the amount of stretching of the tendons in this region. These devices are somewhat helpful but most often do not provide nearly enough pressure, due to their design, to prevent trauma in this region. Prior art devices that place pressure on the epicondyle simply do not appreciate the effect of reducing or dissipating the shock energy which exits via the elbow.

The better approach is to localize the pressure and increase it to prevent the tendons of interest from stretching or pouching. Also, it would be preferable to somehow absorb the shock energy which exits via the elbow in order to reduce the amount of trauma that can be caused to the tendons and tissues in the areas surrounding the epicondyle. By merely pressing a hardened object against the epicondyle, or wrapping it with an elastic band, little, if any, shock is actually absorbed by these elements, thus ultimately diminishing their ability to alleviate trauma caused by the shock.

Therefore, there is a need for a new device and method which will prevent or alleviate the condition known as tennis elbow which eliminates the disadvantages and shortcomings associated with prior art devices. Preferably, the device should be lightweight and relatively simple in construction to allow the user to wear it without much impediment during play. It should also be designed so that the device can be simply placed on the arm and easily fixed into place allowing the various elements to perform their designated function with a minimal need to continually maneuver and maintain the elements at their proper location on the arm.

SUMMARY OF THE INVENTION

The present invention eliminates many of the disadvantages attributable to prior art devices by providing a novel elbow brace that dissipates a portion of the shock energy that can be generated and travel along the forearm of the player and exits the player's elbow during physical activity, thus reducing the amount of trauma suffered by the tendons in the elbow region. The invention also applies direct pressure to the tendons that are vulnerable to the abnormal stretching which brings on the inflammation associated with tennis elbow.

In general terms, the present invention is directed to a novel elbow brace construction that utilizes a pair of shock absorbing elements that are placed on the arm over the medial and lateral epicondyle of the humerus bone. These shock absorbing elements are made from an absorbent rubber or rubber-like material, which can provide a means for absorbing the shock energy and vibration which are associated with the physical activity that can promote tennis elbow. The device also includes a pressure transmitting element which is designed to impart a localized and direct amount of pressure onto specific tendons that are more vulnerable to stretching and developing tennis elbow and its associated inflammation and discomfort. In one form of the invention, a pressure transmitting element is designed to localize pressure directly onto the tendon that extends from the extensor digitorum muscle and is attached to the humerus. In another form of the invention, another pressure transmitting element can be placed in contact with the arm directly over the tendon of the triceps brachii which is attached to the olecranon of the ulna.

These pressure transmitting elements provide a sufficient amount of radial force or pressure on these particular tendons to prevent them from pouching during physical activity. As a result, the trauma and stretching that occurs during the physical activity are diminished thus resulting in a prevention or an attenuation of the condition known as tennis elbow.

In one particular form of the invention, the shock absorbing elements comprise a pair of washer-like rings made of the shock absorbing material. Each ring is placed over the epicondyle of the humerus in such a manner as to allow the shock absorbing material to surround the epicondyle where the tendons are attached. The ends of the tendons which are susceptible to the inflammation are in contact with a shock absorbing material which allows for absorption of the shock energy that may be transmitted along the forearm to the elbow region. As a result, the shock absorbing material transmits the energy away from the elbow thus reducing the amount of trauma suffered by the tendons in the epicondyle area.

In another particular form of the invention, the pressure transmitting elements may be comprised of generally elongate tubular members which extend approximately the length of the tendons that they contact. This particular structure is beneficial during play since the tubular members are generally disposed within an elastic sleeve-like member which includes pouches or pockets which house the tubular members. The tubular members remain in place within the pockets during play and in proper contact with the region of the arm where the pressure is to be applied. Their configuration maintains them in direct contact with the tendons during play since the same amount of surface area contacts the tendon throughout play, even if the elements should rotate within the pocket. The tubular members can also be hollow to allow for some shock absorbing capability during the physical activity.

The features and advantages of the present invention will become more apparent from the foregoing detailed description taken in conjunction with the accompanying drawings which illustrate by way of example the principle of the present invention.

BRIEF DESCRIPTION OF THE DRAWINGS

FIG. 1 is a perspective view of one embodiment of an elbow brace made in accordance with the present invention as it is placed on the arm of a user and showing in phantom lines the elements that are disposed on the brace and in contact with the arm.

FIG. 2 is another view of the elbow brace depicted in FIG. 1 which shows a cutout portion showing one of the shock absorbing elements.

FIG. 3 is a view of the elbow brace depicted in FIG. 1 showing a backside view of the elbow and a cut away portion which shows the placement of one of the pressure transmitting elements as it applies pressure to the tendon of the triceps brachii.

DETAILED DESCRIPTION OF THE PREFERRED EMBODIMENT

Figure 4:
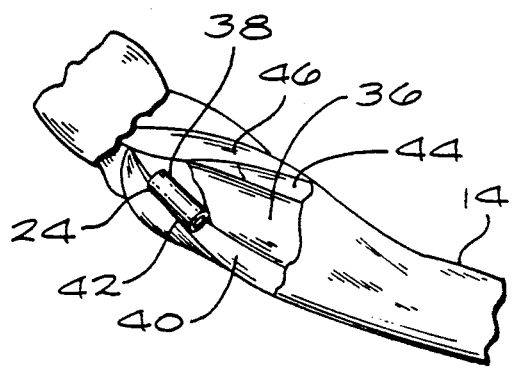
FIG. 4 is a view showing a cut away portion of an arm which shows the various muscles and tendons of the forearm along with a pressure transmitting element which applies pressure to the tendon of the extensor digitorum muscle.

The present invention provides a novel approach in preventing or attenuating the effects of tennis elbow by providing an elbow brace and method for simultaneously applying both pressure to injury sensitive tendons in the elbow region along with the application of a shock absorbing medium to dissipate a portion of the shock energy that may effect the elbow region and cause trauma to the injury prone tendons found therein. As a result, the present invention creates a more advantageous device and method over the prior art since the critical body members are less susceptible to the effects of pouching of the tendons and the shock energy which produces much of the damage to the tendons and tissue in the elbow region.

FIG. 1 shows one particular embodiment of an elbow brace made in accordance with the present invention. The elbow brace 10 is shown as it is affixed to the arm 12 of a user covering both the forearm 14, elbow region 16, and upper arm 18. FIG. 1 shows in phantom lines the various elements which are designed to impart the pressure onto the various tendons of the arm along with the elements which provide the shock absorbing features which absorbs a good portion of the shock energy in the elbow to reduce the inflammation of the tendons at the epicondyle.

The elbow brace 10 shown in FIG. 1 includes a first shock absorbing element 20 which is in contact with the arm and is placed directly over the medial epicondyle of the humerus bone. A second shock absorbing element 22 is also located on the elbow brace 10 and is in contact with the arm and located directly over the lateral epicondyle of the humerus bone. For the sake of clarity, FIGS. 1-3 do not show either the medial or epicondyle bone in the arm, however, it must be appreciated that these members are placed directly over the specific regions in the arm to provide the shock absorbing capabilities necessary to dissipate the trauma and inflammation caused by the shock energy which travels to and exits the elbowregion.

The elbow brace 10 also includes a first pressure transmitting element 24 which also contacts the forearm 14 of the arm and is placed directly over the tendon of the extensor digitorum muscle which is attached to the humerus. (See FIG. 4.) A second pressure transmitting element 26 is also found on the elbow brace 10 on the back side of the arm where it contacts the arm directly over the tendon of the triceps brachii which is attached to the ulna bone. FIG. 3 shows a partial cut away view which shows this second pressure transmitting element 26 as it is placed in relationship to the tendon of interest. FIG. 5 also shows the muscle and tendons of the triceps brachii and will be further discussed in greater detail below.

The elbow brace 10 can be manufactured from a tubular sleeve-like elastic member 28 which also helps impart a slight inward radial pressure on the arm. This type of sleeve-like member 28 can also help impart some pressure onto the outer surface 30 (FIG. 2) of the first and second shock absorbing elements to apply a small amount of pressure to the tendons in the area of the medial and epicondyle area. The elastic nature of the brace can also help maintain the various elements in direct contact with the arm to enable the elements to perform their particular functions. It should be noted that in FIGS. 1, 2 and 3, the pockets or pouches which house these particular elements 20, 22, 24 and 26 are not shown in great detail but are shown in cross-sectional view in FIGS. 6 and 7. It should be appreciated that the tubular sleeve-like member which forms the portion of the elbow brace can be, for example, a double piece of fabric which has stitching which provides and creates the internal pockets which house the shock absorbing and pressure transmitting elements. Other arrangements could be made in which individual pockets are formed on a single layer of elastic material which forms the brace. Clearly, there are any number of different possibilities in creating the particular means for holding and maintaining the shock absorbing and pressure transmitting elements at the respective locations on the arm.

In the particular embodiment disclosed in FIGS. 1-3, the first and second shock absorbing elements 20 and 22 are shown as ring-like members which are made from a shock absorbing material which is particularly designed to absorb much of the shock that may be transmitted along the forearm of the player during athletic activity or other related activities. These shock absorbing elements are placed directly over the medial and lateral epicondyle such that the shock absorbent material actually surrounds the tip of the epicondyle and contacts the region around the tip where many of the tendons of the forearm are attached. The ring-like member construction allows the tip of the epicondyle to extend into the opening 30 defined therein since no appreciable amount of tendons are actually attached at the central tip. The absorbent material, rather, remains in contact with the soft tissue and the tendons attached around the epicondyle to absorb the shock that gets dissipated at the elbow region. The shock absorbing characteristics of these first and second shock absorbing elements helps transmit the shock away from the elbow region thus reducing the amount of trauma that can be caused to the tendons and tissue at the elbow region.

The first and second pressure transmitting elements 24 and 26 depicted in FIGS. 1-3 are shown as generally hollow, elongate tubular members which are made from a plastic material which allows for some shock absorbing capabilities as well. These shock absorbing elements produce an inner radial force onto the tendons of interest and are again held in place by the tubular sleeve-like member. In fact, the tubular sleeve-like member also helps impart the force that is placed on the tendons of interest since the tubular member must have a snug fit on the arm to allow the pressure transmitting elements to contact the arm and apply the inward radial pressure. These pressure transmitting elements each provide a certain amount of surface area which contacts the arm of the player and defines an area of contact which allows the brace to direct pressure to the specific tendons of interest. The placement of the pressure transmitting elements, as well as the shock absorbing elements, is critical since a misalignment of these elements of the arm will not allow the elements to perform the necessary functions to the particular body parts.

Figure 6:
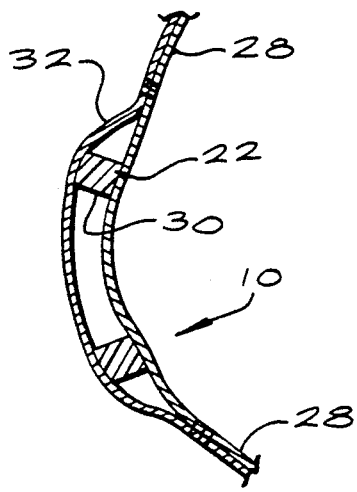
FIG. 6 is a cross-sectional view of one of the shock absorbing elements contained within a pocket of the tubular elastic sleeve-like member.
Figure 7:
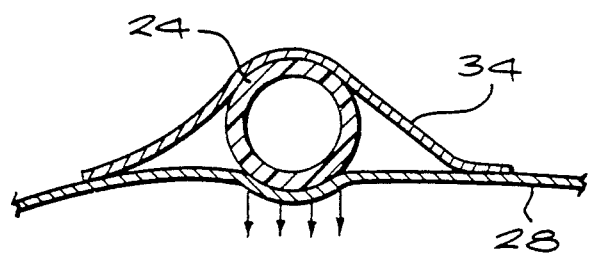
FIG. 7 is a cross-sectional view showing a pressure transmitting element contained within a pocket of the tubular elastic sleeve member.

The use of the tubular sleeve-like member in the embodiment shown herein is particularly useful since the pockets formed in the brace maintain the various elements at the desired location on the arm. Referring now to FIGS. 6 and 7, these pockets 32 and 34 prevent the elements from slipping from the locations on the arm and also help place the elements in the right positions on the arm. For example, when the brace is initially placed on the arm, the user only has to place the shock absorbing elements over the respective epicondyle of the humerus bone and the pressure transmitting element will automatically find its intended spot on the arm over the tendons of interest. During play, it is possible for the brace to start to move on the arm, which can cause the elements to move from their intended locations on the arm. The user merely has to again realign the shock absorbing elements on the epicondyle (a simple and quick task) and all of the elements of the brace should be in place. The placement of the pressure transmitting elements is fixed with respect to the shock absorbing elements via the sleeve-like member to thus provide the correct placement of these elements on the arm whenever the shock absorbing elements are aligned. As a result, the player need not worry about specially aligning the pressure transmitting elements during play.

Again, referring to FIG. 6, one of the pockets 32 which stores a shock absorbing element is depicted. In this particular figure, the pocket 32 and shock absorbing element 22 are shown in a somewhat distorted shape since the brace is able to conform to the body structure of the user. For example, as is shown in FIG. 6, the shock absorbing element 22 is somewhat bent to show that the element can conform to surround the epicondyle of the user. The sleeve-like member 28 has an excess of material in this pocket region to allow the tip of the epicondyle to move into the opening 30 formed on the shock absorbing element. This structure allows the ring-like member to be positioned correctly on the arm.

Referring now to FIG. 7, the pocket 34 which houses the pressure transmitting element 24 is also shown. In this particular figure, the pressure transmitting element 40 shows how it can contact the surface of the arm and extend inward to provide an inner radial force (shown by the arrows) onto the tendon of interest. The surface area of the tubular member remains constant throughout play, even if the member should start to rotate within the pocket. Thus, this particular configuration of the pressure transmitting element provides an adequate area of surface contact to apply the necessary pressure onto the tendon. It maintains this same amount of surface area in contact with the arm throughout play. If ever the tubular member rotates within the pocket, the same amount of surface area and pressure should still be in contact with the arm and tendon of the user.

Figure 5:
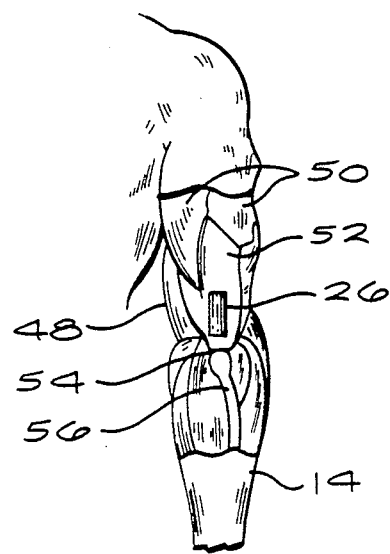
FIG. 5 is an side elevation view showing a partially cut away view of the muscles and bone of the arm which shows a pressure transmitting element in contact with the tendon of the triceps brachii.

Referring now to FIGS. 4 and 5, the particular tendons which are of interest to the pressure transmitting elements are shown in greater detail. First, in FIG. 4, the muscle of the extensor digitorum muscle 36 is shown as it extends through the forearm 14 of the user from the hand (not shown) and as it is attached at the elbow region. This particular muscle 36 also includes a tendon 38 which is the part which is actually attached to the humerus bone (not shown). The other muscles in the forearm include the extensor carpi ulnaris 40 which also has a tendon 42 which is adjacent to the tendon 38 of the extensor digitorum muscle 36. In fact, the first pressure transmitting element can be made sufficiently large enough to contact both the tendon of the extensor digitorum muscle along with the tendon of the extensor carpi ulnaris muscle. The other muscles include the extensor carpi radialis longus 44 and the brevis 46. These muscles and the particular tendons associated with them are generally not affected by the present invention.

Referring now to FIG. 5, the back side 48 of the arm is shown to better illustrate the particular tendon which the second force transmitting element 26 is designed to contact. In FIG. 5, the triceps brachii 50 are shown including a large tendon 52 which is attached to the olecranon 54 of the ulna bone 56 found in the forearm 14 of the user. This particular tendon 52 is of interest and concern since it too can become stretched and inflamed from the vibrational forces and shock energy which can cause the condition known as tennis elbow. Generally, the second pressure transmitting element 26 does not have to extend along the entire length of the tendon, but rather can be placed in the region adjacent to the attachment to the olecranon 54. This is due to the fact that much of the force and stretching will occur in this particular region.

Figure 8:
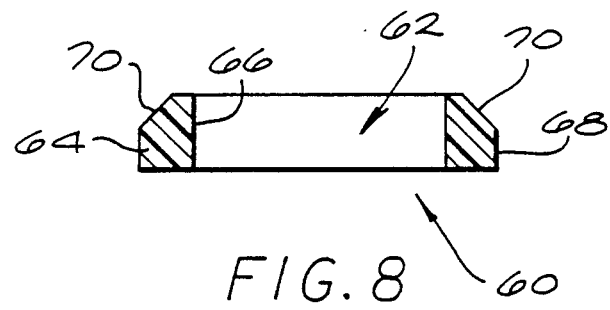
FIG. 8 is a cross-sectional view of one embodiment of the shock absorbing element.

Referring now to FIG. 8, one particular form of the shock absorbing element 60 is shown in a cross-sectional view in which the ring-like member includes an opening 62 and a ring of absorbent material 64. This particular ring 60 includes an inner diameter which defines an internal surface 66 and an external surface 68. The external surface 68 includes a taper portion 70 which tapers inward toward the inner diameter. Generally, the surface 70 would contact the arm and the taper 70 of the ring would extend away from the elbow. This particular taper 70 is advantageous since it helps direct shock energy away from the elbow.

The method for preventing or attenuating the effects of tennis elbow utilizes the same principles of applying pressure and shock absorbing materials to the specific body areas of the user. This method includes the placement of the shock absorbing material or elements directly over the medial and lateral epicondyle of the humerus bone along with the direct localized pressure which is applied to the tendons of the extensor digitorum muscle and the triceps brachii muscle. The materials utilized in the method depict the shape and form of the elements shown as the shock absorbing and pressure transmitting elements depicted in FIGS. 1-8. Additionally, it should be appreciated that different shaped elements could be utilized in the method to achieve the same function of applying shock absorbing material to the elbow region along with pressure to the tendons of interest. Such changes would certainly be within the spirit and scope of the present invention.

The shock absorbing elements can be generally made from a rubber or rubber-like material having a hardness substantially within the range of 40 to 60 Shore hardness. If materials having drastically different densities are utilized, then it is possible that the shock absorbing elements will not provide the sufficient amount of shock absorbing capabilities necessary to reduce the trauma in the elbow region. If the material density or hardness is too little, then the shock energy again will not be sufficiently absorbed and dissipated. It should be appreciated that the materials need not be rubber but can be any material which provides the appropriate amount of shock absorbing capability associated with materials with the specific range of hardness which falls within the range herein identified. Again, the critical factor is that the epicondyle be placed in contact with a shock absorbing material which will dissipate a good portion of the shock energy that may be transmitted through the forearm to the elbow region.

From the above, it is evident that the present invention provides a novel approach for an elbow brace and method for preventing and attenuating the symptoms and pain associated with the condition known as tennis elbow. The elbow brace and method described above are superior over the prior art since the present invention provides both shock absorbing and pressure transmitting capabilities to the body parts which are most affected by the shock energy and the stretching of the tendons which causes tennis elbow. While particular forms of the invention have been described and illustrated, it will also be apparent to those skilled in the art that various modifications may be made without departing from the spirit and scope of the invention. Accordingly, it is not intended that the invention be limited except by the appended claims.

What is claimed is:

1. An elbow brace for preventing or attenuating tennis elbow comprising:
   first and second shock absorbing elements;
   first and second pressure transmitting elements;
   means for maintaining said first and second shock absorbing elements and said first and second pressure transmitting elements in contact with the arm of the user;
   said first shock absorbing element adapted to be placed in contact with the arm of the user directly over the medial epicondyle of the user when held in position by said means for maintaining;
   said second shock absorbing element adapted to be placed in contact with the arm of the user directly over the lateral epicondyle of the user when held in position by said means for maintaining;
   said first pressure transmitting element adapted to be placed in contact with the arm of the user so as to apply pressure to the tendon that extends from the extensor digitorum muscle and is attached to the humerus of the user when said first pressure transmitting element is held in position by said means for maintaining;
   and said second pressure transmitting element adapted to be placed in contact with the arm of the user so as to apply pressure to the tendon that extends from the triceps brachii muscle and is attached to the olecranon of the user when said first pressure transmitting element is held in position by said means for maintaining.

2. The elbow brace as defined in claim 1 wherein said maintaining means comprise a tubular plastic sleeve member including means for holding said shock absorbing elements and said pressure transmitting elements to said sleeve-like member.

3. The elbow brace as defined in claim 2 wherein said holding means comprise pockets affixed to said sleeve-like members for housing each of said shock absorbing and pressure transmitting elements.

4. The elbow brace as defined in claim 3 wherein said maintaining means also applies pressure to each of said shock absorbing elements to direct some pressure to the tendons surrounding the lateral and medial epicondyle.

5. The elbow brace as defined in claim 4 wherein each of said shock absorbing elements has an outer peripheral region which is adapted to surround and contact the epicondyle.

6. The elbow brace as defined in claim 5 wherein each of said shock absorbing elements comprise a ring-like member having an internal opening and a periphery of shock absorbing material adapted to encircle the epicondyle.

7. The elbow brace as defined in claim 6 wherein said ring-like member has an internal and external diameter, the surface defined by the external diameter being tapered to help transmit shock energy away from the epicondyle.

8. The elbow brace as defined in claim 7 wherein each of said shock absorbing elements are adapted to transmit at least a portion of shock energy that may be transmitted along the forearm away from the epicondyle.

9. The elbow brace as defined in claim 8 wherein said shock absorbing element is made from rubber or a rubber-like material having sufficient density to absorb at least a portion of shock energy that may be transmitted along the ulna of the user.

10. The elbow brace as defined in claim 9 wherein said shock absorbing element is made from a material having a Shore hardness of about 40 to 60.

11. The elbow brace as defined in claim 10 wherein said first pressure transmitting element also applies pressure to the tendon that extends from the extensor carpi ulnaris muscle and is attached to the humerus bone of the user.

12. The elbow brace as defined in claim 11 wherein said pressure transmitting elements also absorb a portion of shock energy that may travel along the forearm of the user.

13. The elbow brace as defined in claim 12 wherein said first pressure transmitting element has a width and length, the length of which runs substantially parallel with the length of the tendon of the extensor digitorum muscle.

14. The elbow brace as defined in claim 13 wherein each of said pressure transmitting elements comprise hollow tubular members.

15. The elbow brace as defined in claim 14 wherein said hollow tubular members are made from a plastic material that is also capable of absorbing shock energy.

16. The elbow brace as defined in claim 15 wherein each of said tubular members has a length that is greater than 1 inch.

17. An elbow brace for preventing or reducing tennis elbow comprising:
   a tubular sleeve like member having a plurality of pockets defined therein;
   a first shock absorbing element disposed within one of said pockets and in contact with the arm of the user directly over the user's medial epicondyle to absorb at least a portion of shock energy that may travel along the user's forearm in order to reduce the amount of shock imparted to the tendons attached to the medial epicondyle;
   a second shock absorbing element disposed within one of said pockets and in contact with the arm of the user directly over the user's lateral epicondyle to absorb at least a portion of shock energy that may travel along the user's forearm in order to reduce the amount of shock imparted to the tendons attached to the lateral epicondyle;
   a first pressure transmitting element disposed within one of said pockets and in contact with the user's arm to impart a direct force onto the tendon that extends from the extensor digitorum muscle and is attached to the humerus of the user, said pressure transmitting element preventing the tendon from extending outward away from the user's ulna; and a second pressure transmitting element disposed within one of said pockets and in contact with the user's arm to impart a direct force onto the tendon that extends from the triceps brachii muscle and is attached to the olecranon of the user, said second pressure transmitting element preventing the tendon from extending outward away from the user's humerus bone.

18. The elbow brace as defined in claim 17 wherein each of said shock absorbing elements comprise a ring-shaped member made from a shock absorbing material which surrounds or encircles the respective epicondyle.

19. The elbow brace as defined in claim 18 wherein each of said pressure transmitting elements comprise a hollow tubular member which has a length of at least 1 inch.

20. The elbow brace as defined in claim 19, wherein the sleeve-like member is made from an elastic material which imparts an inward radial force on the arm of the user.

21. A method for preventing or reducing tennis elbow comprising:
   positioning a shock absorbing material against the arm of the person so that the material surrounds the person's medial and lateral epicondyle;
   applying direct pressure on the tendon that extends from the extensor digitorum muscle to the humerus of the person to prevent that tendon from moving outward away from the person's ulna; and
   applying direct pressure on the tendon that extends from the triceps brachii and is attached to the olecranon to prevent that tendon from extending away from the humerus.

22. The method as defined in claim 21 further including the step of maintaining the shock absorbing material and the pressure on the tendons when the person is engaged in physical activity.

* * * * *